United States Patent [19]

Garreau et al.

[11] Patent Number: 5,175,773
[45] Date of Patent: Dec. 29, 1992

[54] METHOD OF THREE-DIMENSIONAL RECONSTRUCTION OF ARBORESCENCE BY LABELING

[75] Inventors: Mireille Garreau, St. Gregoire; Alain Bouliou; René Collorec, both of Rennes; Jean-Louis Coatrieux, Le Verger, all of France

[73] Assignee: General Electric CGR S.A., Issy Les Moulineaux, France

[21] Appl. No.: 659,406
[22] PCT Filed: Sep. 7, 1989
[86] PCT No.: PCT/FR89/00449
    § 371 Date: Apr. 23, 1991
    § 102(e) Date: Apr. 23, 1991
[87] PCT Pub. No.: WO90/03010
    PCT Pub. Date: Mar. 22, 1990

[30] Foreign Application Priority Data

Sep. 13, 1988 [FR] France .................. 88 11917

[51] Int. Cl.⁵ ............................................ G06K 9/00
[52] U.S. Cl. .............................. 382/6; 364/413.16;
                                      364/413.19; 382/54
[58] Field of Search ................... 382/6, 54, 30;
       364/413.13, 413.15, 413.16, 413.19, 413.22;
                                                   358/111

[56] References Cited

U.S. PATENT DOCUMENTS

| | | | |
|---|---|---|---|
| 4,436,684 | 3/1984 | White | 382/6 |
| 4,672,651 | 6/1987 | Horiba et al. | 364/414 |
| 4,771,467 | 9/1988 | Catros et al. | 382/6 |
| 4,843,629 | 6/1989 | Mischler et al. | 382/6 |
| 4,945,478 | 7/1990 | Merickel et al. | 382/6 |
| 5,034,987 | 7/1991 | Fujimoto et al. | 382/6 |
| 5,058,176 | 10/1991 | Shimazaki et al. | 382/6 |

FOREIGN PATENT DOCUMENTS 0226507 6/1987 European Pat. Off. .

OTHER PUBLICATIONS

Systems and Computers in Japan, vol. 17, No. 1, Jan. 1986, Scripta Technica, Inc. (N.Y., US), S. Iwai et al.: "3-D reconstruction of coronary artery from cine-angiograms based on left ventricular model", pp. 26-34.
Japan Annual Reviews in Electronics, Computers & Telecommunications, Computer Science & Technologies, 1982, S. Tsuji et al.: "Knowledge-based identification of artery branches in cine-angiograms—an image understanding system which utilizes production-type knowledge", pp. 311-321.
Proceedings of the 5th International Conference on Pattern Recognition, Dec. 1-4, 1980, Fla., vol. 1, IEEE, (N.Y., US), T. Fukui et al.: "Detection and tracking of blood vessles in cine-angiograms", pp. 383-385.
IEEE Transactions on Pattern Analysis and Machine Intelligence, vol. PAMI-6, No. 6, Nov. 1984, IEEE, G. Medioni et al.: "Matching images using linear features", pp. 675-685.
IEEE Transactions on Pattern Analysis and Machine Intelligence, vol. PAMI-8, No. 2, Mar. 1986, IEEE, S. A. Stansfield: "ANGY: a rule-based expert system for automatic segmentation of coronary vessels from digital substracted angiograms", pp. 188-199.
Computers in Cardiology, Oct. 7-10, 1986, Boston, Mass., US, IEEE, Y. Sun et al.: "A hierarchical search algorithm for identification of coronary artery contours in digital angiograms", pp. 583-586.
Pattern Recognition, vol. 17, No. 5, 1984, Pergamon Press, Ltd, (GB), P. Kaufmann et al.: "Visual inspection using linear features", pp. 485-491.

Primary Examiner—Joseph Mancuso
Attorney, Agent, or Firm—Nilles & Nilles, S.C.

[57] ABSTRACT

In order to reconstruct an angiographic arborescence, two images are acquired according to orientations substantially perpendicular to each other of an arborescence (IVA,CX) to be reconstructed. By a follow-up operation of the segments, the coordinates of the arborescence segments are reconstructed. Indeterminations resulting from the too small number of acquisitions effected are removed by emitting hypotheses (AV, IV) on forms deductible from the recorded acquisitions and by verifying those hypotheses with respect to a model. The model has the particularity of being structural, that is to say substantially descriptive. In this structural model, each arborescence segment is characterized by a number, by a direction (49-54), and by the numbers, direction and number of segments preceding or following it. By operating in this way, it has been proved that angiographic images may be reconstituted in a more rapid and simple way.

17 Claims, 6 Drawing Sheets

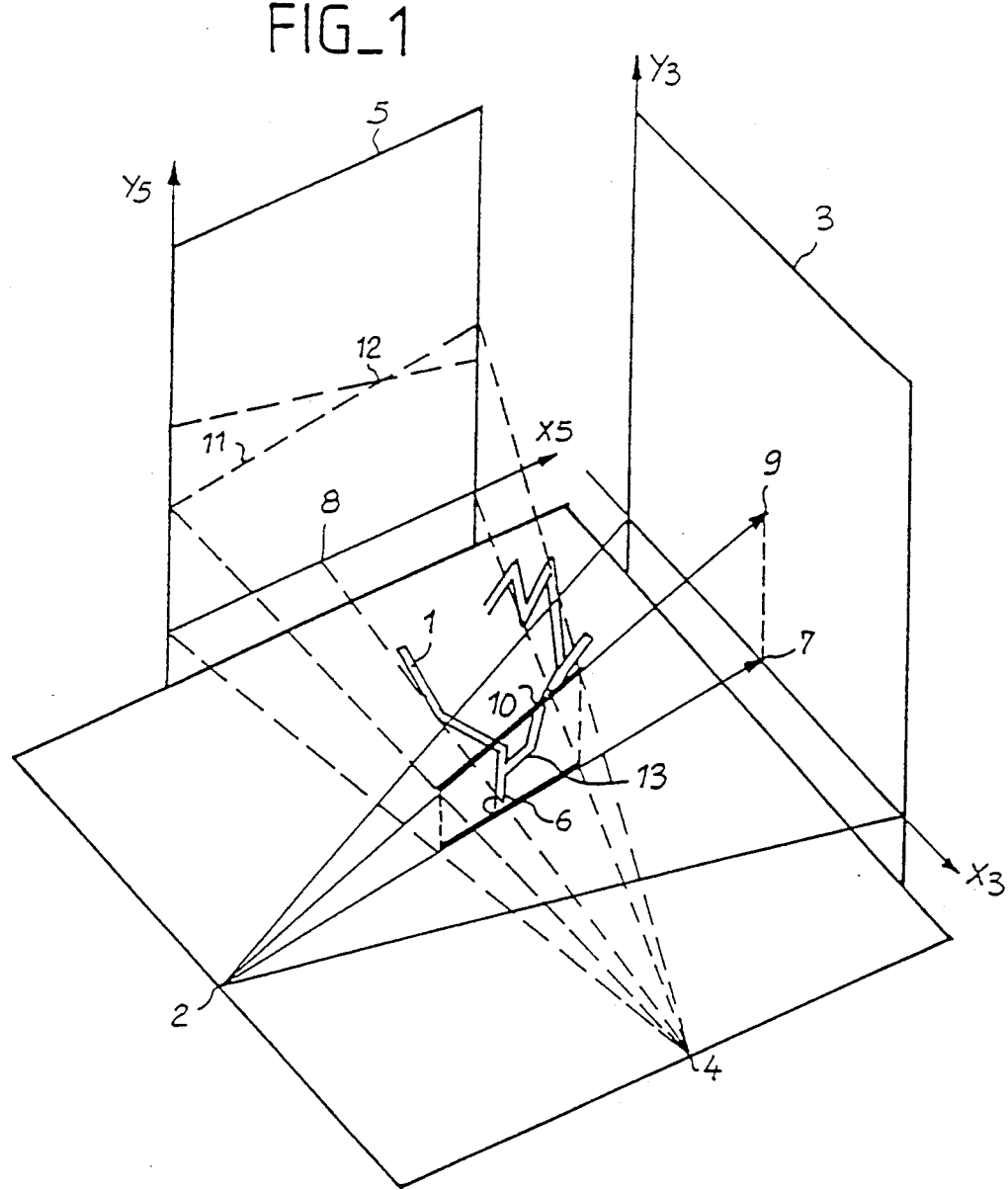
FIG_1
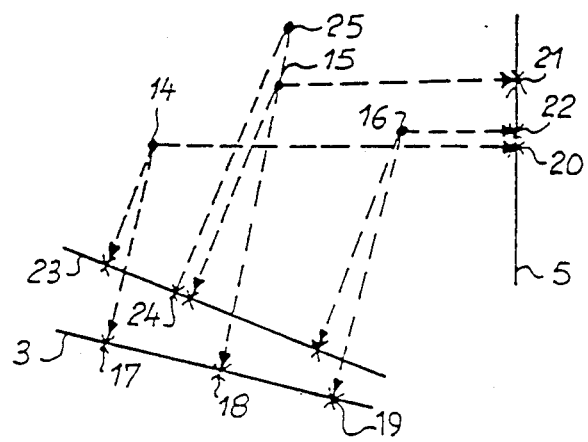
FIG_2

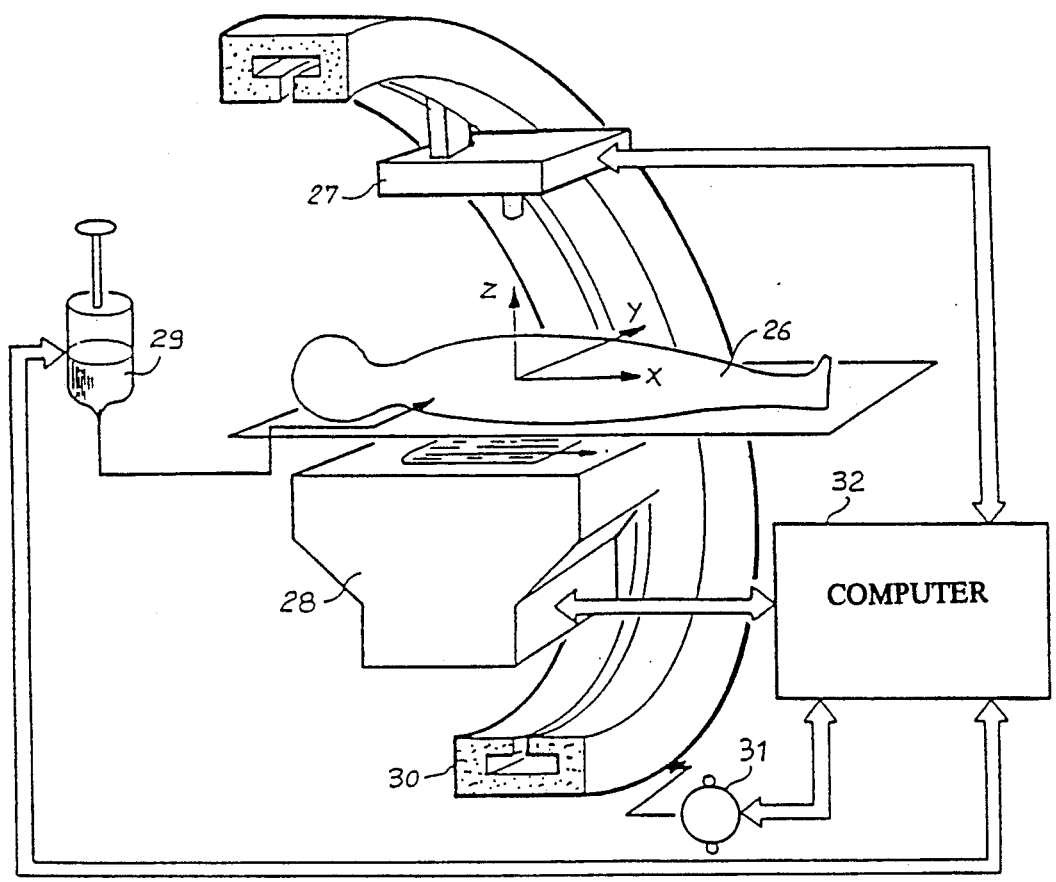
FIG 3
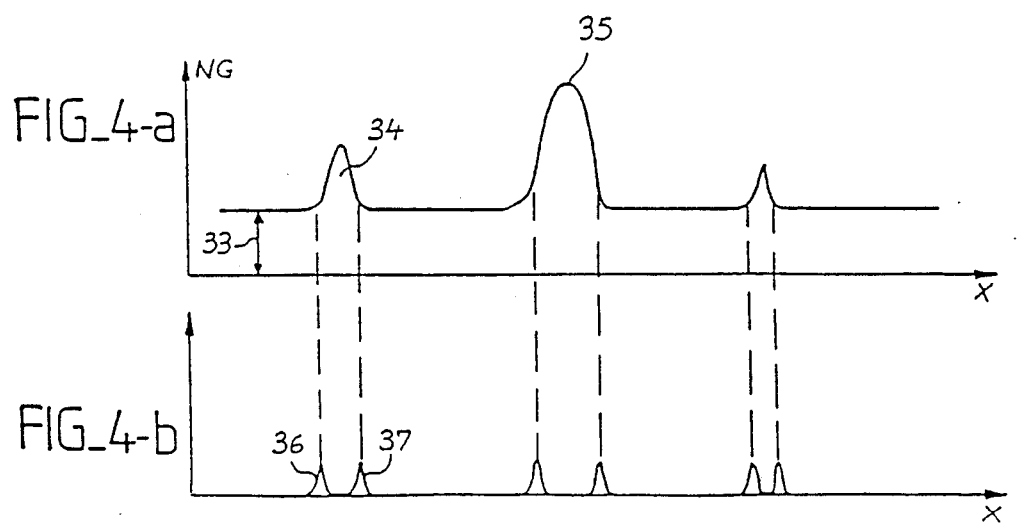
FIG_4-a
FIG_4-b

FIG_5
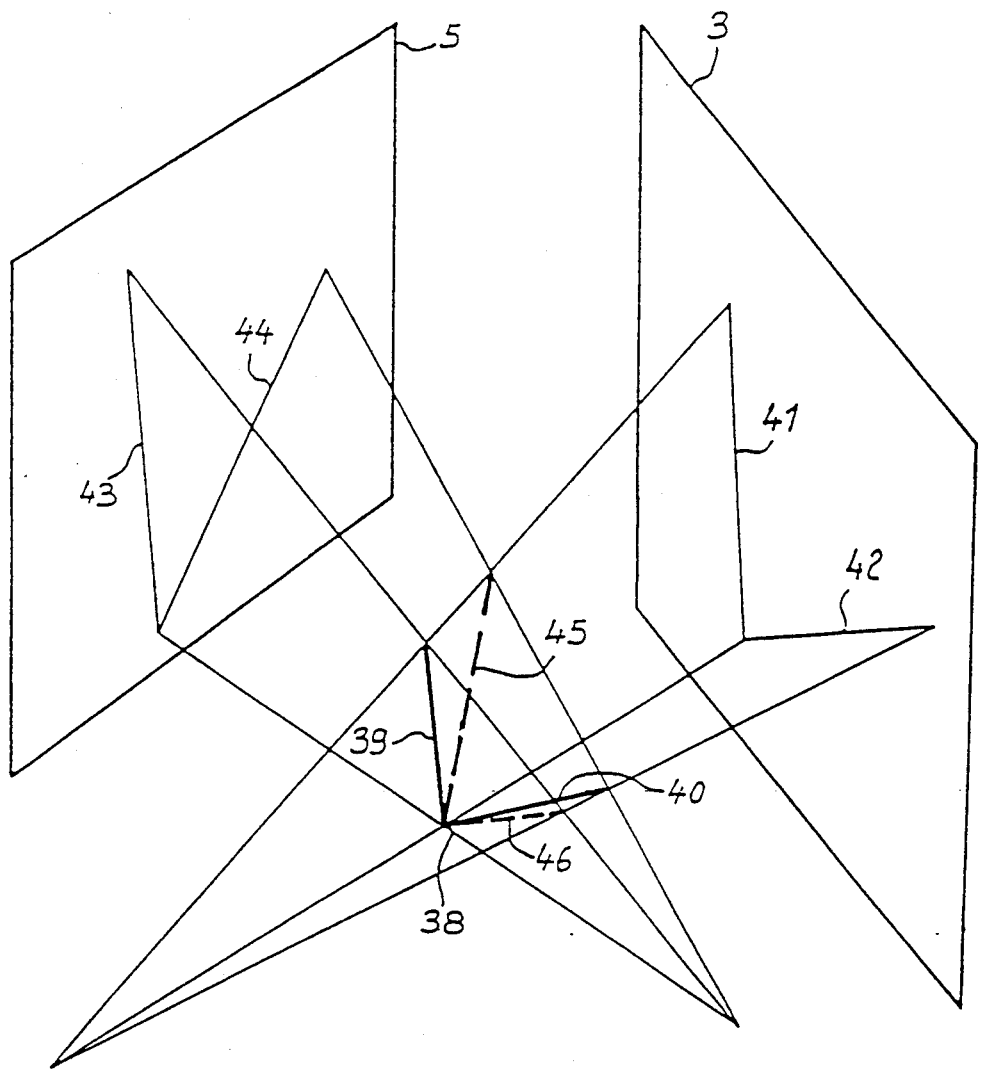

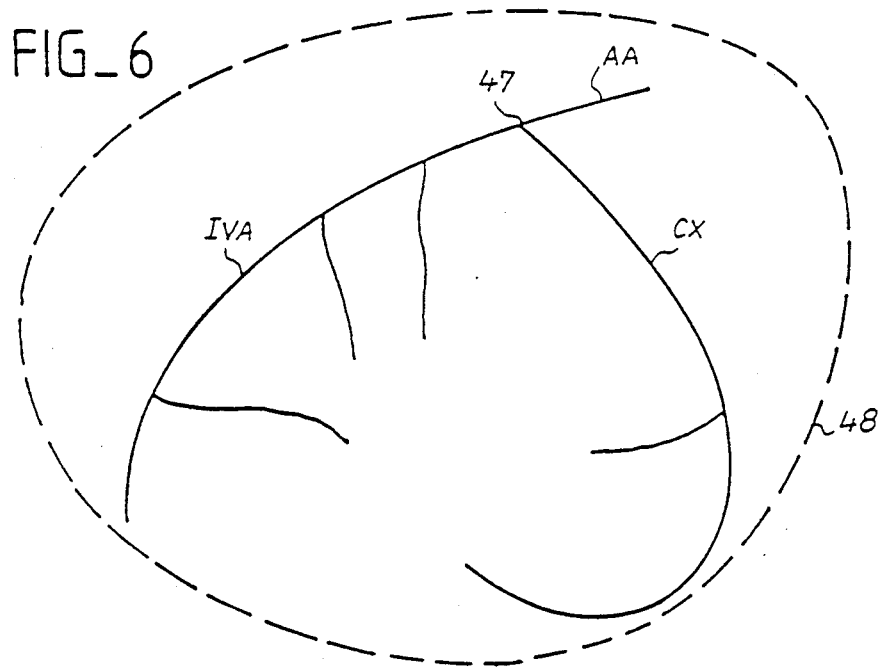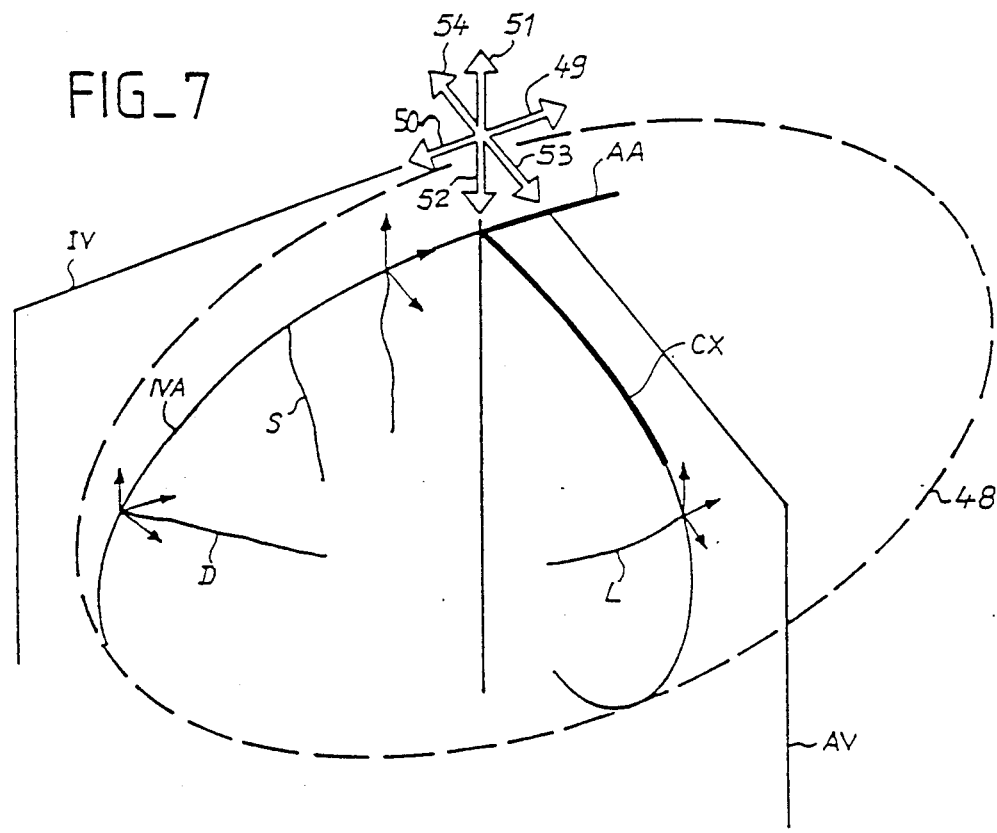

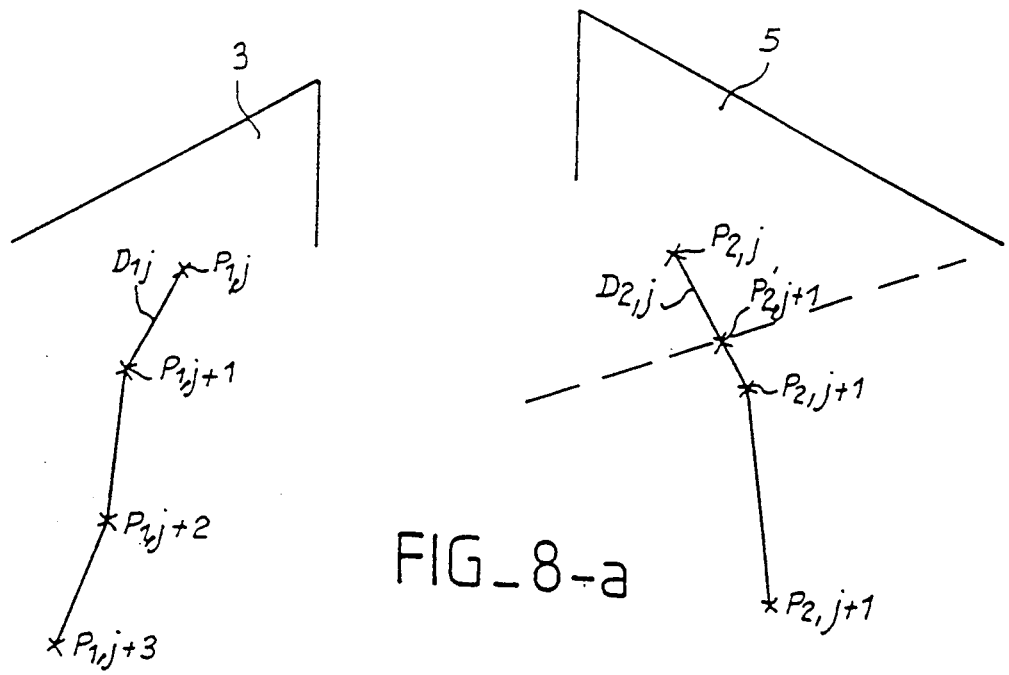
FIG_8-a
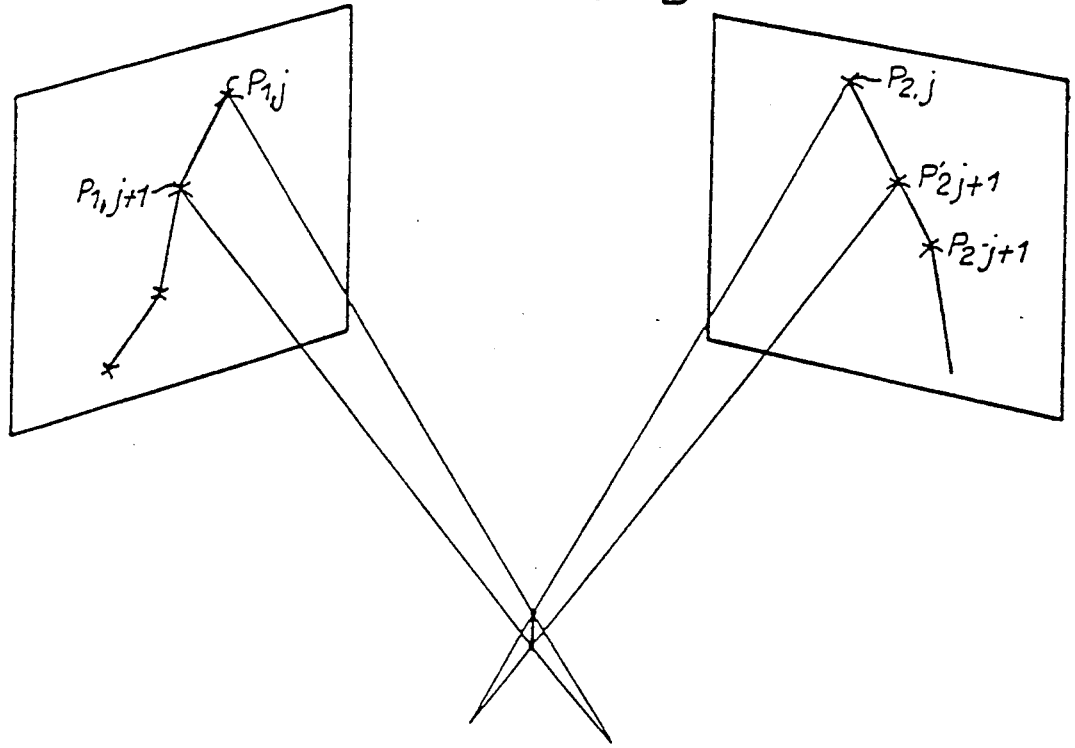
FIG_8-b

FIG_9
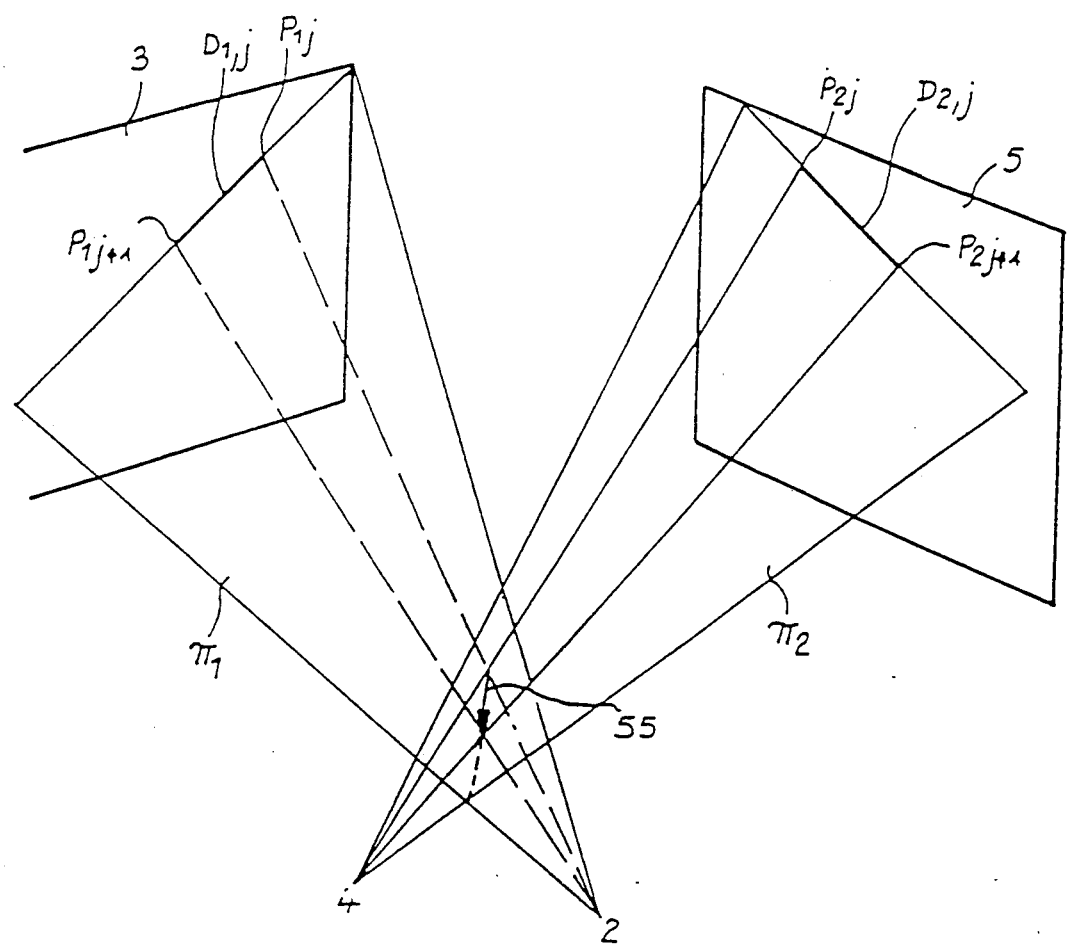

METHOD OF THREE-DIMENSIONAL RECONSTRUCTION OF ARBORESCENCE BY LABELING

BACKGROUND OF THE INVENTION

1. Field of the Invention

The present invention relates to a method of three-dimensional (3D) reconstruction of arborescence by labeling. The invention is primarily intended to be employed in the medical field in which the arborescences studied are angiographic arborescences. By subsequent processing of information on the reconstructed object, three-dimensional reconstruction makes it possible to present the object in any desired mode: transverse cross-sections, oblique cross-sections or even 3D display. It should be added that 3D display of 3D objects is already known The invention is essentially concerned with acquisition of geometrical data which are representative of a 3D arborescence, these data being subsequently employed in methods of visualization for displaying the arborescence. The distinctive feature of the method in accordance with the invention is that it permits reconstruction of arborescences from two-dimensional digital images in projection of the object to be reconstructed The field of application of the invention is in particular the study of the vascular system (arterial and venous system) of any region of the human body which has a treelike structure (heart, brain, femoral artery, carotid artery, etc.). The mode of acquisition of images in projection is independent of the method. Although the invention is described in a radiology application, this latter is transposable to the case in which the images by projection are obtained by NMR, by ultrasonic insonification, and so on. Digital or analog radiology by x-rays (angiographic technique) makes it possible at the present time to obtain images which are well-suited to the practical application of the invention. The method in accordance with the invention is also applicable to any 3D filar structure other than medical.

2. Discussion of the Background

Current angiographic reconstruction techniques consist partly of techniques derived from tomodensitometric experimentation involving the use of scanners. However, the corresponding acquisitions are complicated, firstly by the need to remove from acquired images the contributions of all that does not represent the angiographic system, secondly by the fact that the flow of blood within the vessels is a phenomenon which is variable with time (and therefore calls for synchronization) and finally by the fact that the acquisition must be a three-dimensional acquisition. In order to eliminate contributions to the images by elements which are foreign to the angiographic system, it is a known practice to utilize injections of products which enhance the contrast within the capillaries. It will be borne in mind, however, that these injections cannot be repeated as often as may be desired without traumatizing the patient. The synchronization phenomenon may have the effect of increasing the duration of acquisitions. At the same time, this technique is contrary to the precautions which are necessary in order to avoid over-frequent injection of the contrast-enhancing product into a patient's blood vessels. Finally, when making use of scanner methods, three-dimensional reconstruction calls for repetition of these experiments. One of the solutions to this problem would consist in employing multi-row multidetectors in the scanners. However, this technique is essentially related to the systematic use of so-called conic projections since the x-ray source remains a point source. The algorithms of reconstruction of cross-sectional images from conic projections do not subsequently make it possible to achieve the requisite precision for permitting reconstructions. In order to overcome this disadvantage, a scanner has been designed to acquire the images of four cross-sections at the same time. The complexity of this machine is clearly multiplied by the number of simultaneous cross-sections which it is desired to acquire.

Scanner acquisition is nevertheless subject to a disadvantage: it takes place in the course of time and, in particular when it is sought to represent moving organs such as the heart, it can finally provide only blurred images of the part of the body to be displayed. In order to avoid problems of synchronization (and resultant multiple injections of contrast-enhancing products), there has been designed an apparatus equipped with fourteen x-ray generators each associated with a camera. Each of the fourteen pairs is then capable of producing an image in projection of the structure to be reconstructed. This system surrounds a volume of the body from which a numerical volume is produced. A numerical volume is a collection of data relating to a measured property and arranged virtually in a volume at 3D addresses corresponding to the locations of the object from which the information is obtained. Interesting results have thus been obtained for the reconstruction of coronaries. This system makes it possible in addition to display all the structures which exhibit an attenuation to x-rays. However, the disadvantages of this system are twofold. In the first place, they are of a technical order: the cost of the equipment is incompatible with industrial diffusion. Furthermore, the definition of the images is not sufficient for detection of fine structures. Should it be desired to obtain a resolution which is adapted to these fine structures, the number of data to be acquired and to be processed over a period of time compatible with medical use imposes an appreciable increase in the power of the machines. In addition, the problem is of a theoretical order: the x-ray beam employed is a divergent beam. The "parallel cross-section" approximation employed for the reconstruction is therefore rough. Utilization of conical geometry in the reconstruction algorithms precludes any possibility of resolving the problem into a superposition of two-dimensional reconstructions.

Another technique has been employed. This technique consists of an algorithmic approach by searching for homologous points. This method consists in determining homologous points on images in projection. Homologous points are points of images of each projection which are associated and which correspond to one and the same point of the 3D space of the arborescence to be reconstructed. The algorithmic method makes it possible to calculate the 3D coordinates of the point of the object from a knowledge of the images acquired and of the geometry of the acquisition system. The methodology employed in this case is as follows. A characteristic point is sought with a first algorithm on a first image in projection. This characteristic point is located on the path of a particular x-ray. The path of the x-ray is known as a "3D straight line". The method consists in projecting the 3D straight line on the second image in projection by making use of the second projection orientation. The homologous point of the characteristic point chosen must be sought in the second image in projection: it must be located on the projected 3D straight line known as an epipolar line.

The most reliable characteristic points for the vascular trees are the points of bifurcation. In fact, the images in projection have patterns which are essentially of two types. In a first type, Y-patterns represent a bifurcation: a main blood vessel is divided into two secondary vessels. In a second type, the patterns represent X intersections: in the majority of cases, these intersections do not correspond to any particular structure within the body. In fact, they are only the result of the projection, on a plane, of two independent segments, only the images of which intersect each other.

Automatic localization of the characteristic points calls for effective segmentation of angiographies. The accuracy which is necessary in the determination of a homologous point in the stereoscopic condition in order to ensure that the estimation of the X, Y, Z coordinates of the corresponding points in the object is acceptable, is less than one pixel. This constraint can be made more flexible if it is possible to increase the angle between shots, between the directions of projection. This can be obtained by making use of views having projection orientations which are spaced at an angle close to 90°.

In a particular version of the method, three images in projection are acquired at orientations included in an angle of 90°. This accordingly solves the principal difficulty of conventional methods which is that of reconciling two opposite constraints in order to obtain sufficient accuracy of the 3D precision of an element of the object. With orientation spacings of the order of 90° between projections, the result thereby achieved is to improve the accuracy of calculation of coordinates of the point of intersection of the straight lines corresponding to the homologous point. On the other hand, by choosing views having small angles of projection with respect to each other, the problem of correspondences between images can be solved. In the final analysis, relinquishment of scanner techniques can lead to simplification of equipments for the reconstruction of arborescence. However, in the last method mentioned above, as also presented in a French Patent Application No. 87 16156 filed on Nov. 23, 1987, it was still necessary to provide three x-ray tube—camera equipments. With these three equipments, one acquires the three images, the projection orientations of which make an angle between them respectively of 90° and of a few tens of degrees.

SUMMARY OF THE INVENTION

The object of the invention is to overcome the aforementioned disadvantages by proposing a method of three-dimensional reconstruction of arborescence in which it is possible to employ only two equipments and in which the absence of the third is compensated by an a priori knowledge of the arborescence to be reconstructed. The two x-ray tube -camera equipments, in a radiology application, are preferably oriented substantially at 90° with respect to each other so as to improve the accuracy of calculation of the point of intersection of the straight lines corresponding to the homologous points. Furthermore, in contrast to models already known for typical arborescent structures, the model of the invention is not a solely topographic model but is an essentially structural model. The expression "topographic model" designates a model in which each part of the object is essentially determined by its coordinates as well as by its dimensions. The expression "structural model" essentially designates a set of data in which each segment of the arborescence is associated with a label which is representative of the number of a bifurcation from which it is derived, or of an upstream segment to which it is connected, as well as an orientation with respect to a reference. In a sense, the structural model is qualitative when the topographic model is quantitative.

It has accordingly become apparent from the foregoing that a structural model of this type made it an easy matter in the first place to remove any reconstruction ambiguities which may result from utilization of only two projections and was well-suited in the second place for the disparity in appearance of the different objects (or individuals) under study. In fact, from this point of view, a topographic model requires highly complex adjustments for changing-over from a small individual to a large individual even if the arborescent structure otherwise retains the same appearance.

The invention is therefore directed to a method of three-dimensional reconstruction of arborescence as distinguished by the fact that it consists:

in acquiring at least a first image and a second image having two dimensions of an arborescence to be reconstructed, these images being obtained by projection of said arborescence in two different orientations, said images being constituted by contiguous segments, in constructing an a priori structural model of the arborescence to be represented, in reconstructing a first segment of the arborescence, in assigning to said first segment a label which is characteristic of a corresponding segment in the model, in checking the correctness of said assignment, and in reiterating the operation for a following segment, and so on in sequence.

BRIEF DESCRIPTION OF THE DRAWINGS

A more complete understanding of the invention will be gained from the following description and from the accompanying drawings which are given solely by way of indication without implying any limitation of the invention. Similarly, the method as described in a radiological application can be transposed to applications in which the acquisitions are of a different type. Likewise, although two images are necessary and sufficient, it is possible to utilize the method of the invention with more than two images. In these drawings:

FIG. 1 illustrates the mode of association of the homologous points;

FIG. 2 illustrates the difficulties encountered when recreating a 3D structure with only two images;

FIG. 3 illustrates a radiology machine for the practical application of the method in accordance with the invention;

FIGS. 4a and 4b are diagrams representing the signals processed in the method in accordance with the invention;

FIG. 5 is a representation of the type of ambiguity which is encountered when utilizing the method in accordance with the invention and the removal of which is permitted by comparison with the model;

FIG. 6 is a known schematic representation of the system of vascularization of the left ventricle of the heart;

FIG. 7 illustrates the model which is derived therefrom in accordance with the teachings of the invention;

FIGS. 8a and 8b illustrate the general mode of reconstruction of the homologous points;

FIG. 9 illustrates the complementary mode in the event of failure of utilization of the general mode.

DESCRIPTION OF THE PREFERRED EMBODIMENTS

FIG. 1 represents the general mode of association of two homologous points. An object 1 to be reconstructed has been subjected in a radiological application to two x-ray illuminations. In a first illumination, the source has been placed at a point 2 and the first image in projection has been formed on a plane 3 perpendicular to the central ray emitted by the source and placed on the other side of the object Similarly, in the second illumination, the source has been placed at 4 and the second image has been projected on a plane 5. The structure 1 is shown in double lines and presents in a simplified manner a foot 6, the image of which has been projected respectively at 7 and 8 on the planes 3 and 5. A luminance intensifier screen coupled with a camera has in fact been placed at the location of the planes 3 and 5. The two pictures have been taken simultaneously whilst a radiological contrast-enhancing product was passing within the structure 1. In a known manner, in order to eliminate the structures which surround the structure 1, it is even possible to carry out a subtraction of images. This means that, in each orientation, two pictures are in fact taken respectively with and without a contrast-enhancing product which passes within the structure 1. By subtracting these two consecutive pictures or images from each other, it is possible in the case of each plane 3 and 5 to observe the appearance of an image resulting from projection of the arborescence 1 alone. It will be considered in the following description that the image of this arborescence alone is available.

The cameras associated with the luminance intensifier screens carry out a horizontal scan oriented along $X_3$ and $X_5$ in each of the two images. It can be postulated that, in the particular case of the foot 6 of the arborescence, it will be readily determined that the homolog of the point 7 whose coordinate $Y_3$ is zero will be a point such that its coordinate $Y_5$ is zero. However, this particular case is in fact the least frequent and it will often be necessary to find the homolog of a particular point 9 which will be the image of a point 10 of the arborescent structure 1. In order to find the homolog of this point, use is made of the fact that the x-ray which has reached the point 9 on the screen 3 was carried by a so-called 3D straight line which passes through point 9 and through the origin 2 of the x-ray emission. The projection in the plane 5 of the 3D straight line which has been found is then drawn from the source 4. This projection 11 is known as the epipolar straight line of the point 9. It is observed that this epipolar straight line is askew with respect to the axes $X_5$ and $Y_5$ of the plane 5. The epipolar straight line normally comprises the point 12 which is homologous to the point 9. These two points 12 and 9 are both representative of the point 10 of the arborescent structure 1. By means of data-processing operations, it is known to calculate the equation of the 3D straight line and to deduce therefrom the equation, in the plane 5, of the epipolar straight line 11. It is then possible to find, among all the points which are representative of the image in projection of the arborescence on the plane 5, the particular point whose coordinates exactly (or most nearly) satisfy the equation of the straight line 11. In principle, if the point 9 in the plane 3 is located on a segment, and if it is not at the intersection of two segments, there is only one candidate point in the plane 5 for which the equation is verified. The same applies if the point 9 is in fact the image of a bifurcation such as, for example, the bifurcation 13 of the arborescence 1.

On the other hand, if the point 9 is placed in the plane 3 at an intersection of two segments, there will normally be found two candidate points in the plane 5 which will satisfy the equation of the epipolar straight line 11. There is therefore an ambiguity. FIG. 2 shows in addition another type of ambiguity resulting from the large angle (if possible close to 90°) which separates the two views. It will in fact be assumed for example that, in the plane $Y_3 = Y_5 = 0$, three points 14, 15 and 16 are identified. The images of these points in the planes 3 and 5 are respectively 17 to 19 and 20 to 22. It is observed that the image 22 of the point 16 has come into an intermediate position between the images of the points 14 and 15 in the plane 5 whereas it was located on their straight line (at 19) in the image on the plane 3. This other type of ambiguity results from the large angle presented by the projections 3 and 5 with respect to each other. In the cited patent Application, this ambiguity was resolved by utilizing another projection, for example on a plane 23 which makes a relatively small angle with one of the two projections. It is noted that the projections of the points 14 to 16 on the plane 23 are arranged in the same order as the order which they had on the plane 3. In the final analysis, a small angle of misorientation of the projections serves to retain the concept of arrangement between the points. However, it is observed that a slight error 24 of appreciation of the coordinates of the image of a point on a projection produces a substantial error 25 in the position of the point to be reconstructed. It will be shown hereinafter how the use of a structural model makes it possible to resolve these ambiguities.

FIG. 3 illustrates a radiology machine for carrying out the method in accordance with the invention. A patient 26 is subjected to x-radiation emitted by a generator 27 in the direction of a luminance amplifier 28 placed on the other side of the patient with respect to the generator 27. A device 29 for injecting contrast-enhancing product is illustrated diagrammatically in order to show that the apparatus is intended to acquire angiography images. It is possible to proceed in two different ways. One possibility (as shown in the figure) consists in subjecting the patient to two successive synchronized irradiations whilst the x-ray tube 27 and the screen 28 have in the meantime been displaced in correspondence on an arch 30 by means of a motor 31 so as to acquire images in which the projection orientation is appreciably different. Orientation differences of the order of 90° are preferably chosen. However, should it be found undesirable to synchronize and if it is desired to avoid the need to reinject a contrast-enhancing product into the patient twice, it may be decided to install on the arch 30 two pairs of equipments 27-28 inclined to each other at a large angle which is preferably a right angle. A computer 32 has the function of managing the acquisition of images, the synchronization, the injection of the contrast-enhancing product as well as a segmentation process for skeletonizing the arborescence in each acquired image.

There can be observed on the luminance intensifier screen 28 the X-orientation of the scan of the associated camera. FIGS. 4a and 4b show in the video-line signal of the camera the waveform of the corresponding grey level signal NG. The subtraction operation is intended to remove the continuous component 33 which is representative of the background in order to leave only signals such as 34 which are representative of the blood vessels alone. The projected image is then, within the memory of the computer 32, a collection of addresses $X_3$ and $Y_3$ with which are associated grey levels ($Y_3$ designates the scanned line) corresponding to the peaks 34 of the detected signals.

In a skeletonization stage, instead of giving consideration to detected points in each image, consideration is given to straight segments to which these different points belong. Each segment can be located in a known manner by applying mathematical morphology or peak-following techniques. It is also possible to determine the contour of the segments. In the skeletonization stage, each segment is given an attribute. This multidimensional attribute indicates the number of the segment, the coordinates of its end points, the mean grey level of the segment, the direction of the segment, and the numbers, numerals, directions and grey levels of the segments which precede and succeed the segment. This skeletonization operation is known and has been described in works already published. In particular, it is described in the thesis by Mrs. Christine Toumoulin defended on Nov. 24, 1987 at the University of Rennes.

In the patent Application cited earlier, with a mathematical morphology technique, consideration was essentially given to following the coordinates of the peaks 3 of the detected signals. The width of the segments in question was then evaluated. This width could preferably be determined by deriving the detected video signal. In this manner, the edges of the vessels under study were shown as peaks such as the peaks 36 and 37 represented in FIG. 4b.

FIG. 5 shows in terms of segments the ambiguities resulting from the use of projections which make a large angle with respect to each other and do not permit certain determination of two homologous points in these two projection planes. The origin of two segments 39 and 40 of the object to be reconstructed has been shown at a bifurcation 38. The segments 39 and 40 are projected respectively at 41 and 42 and 43 and 44 on the above-mentioned planes 3 and 5. If one draws the two dihedrons which pass through the projection sources 2 and 4 and through the segments 39 and 40, it is apparent that these dihedrons intersect at the location of the object to be reconstructed in two other fictitious segments 45 and 46. It is evident that the segments 45 and 46 are also a "solution" for the projection in image segments 41 and 42 and 43 and 44. The utilization of the model in accordance with the invention makes it possible to remove this ambiguity and is accordingly qualitative. It consists in principle in observing that the segments 39 and 40 do not at all have the same orientations in space as the segments 45 and 46. In the invention, it is noted that the segments 39 and 40, taking account of their numerals, of the numeral of their predecessor, are intended to represent two standard segments of a normal anatomic model.

The normal anatomic model is therefore compared on the one hand with the pair of segments 39 and 40 and on the other hand with the pair of segments 45 and 46. Qualitatively, it becomes possible to remove from these pairs the candidate pair which fails to conform to the model. In practice, one label is assigned to each pair in turn and it is ascertained whether the assigned label corresponds to their real shape.

FIG. 6 is a view in perspective providing, in the case of the left ventricle, a representation of the anterior-interventricular artery AIV and of the circumflex artery CX connected in a common trunk to the aortic artery AA via a bifurcation point 47. In accordance with the known topographic models, the AIV artery and CX artery are considered to be located at the surface of an ellipsoid 48. This topographic representation is unfortunately ill-suited to the disparities presented by different individuals and makes it impossible to establish simple criteria which permit automatic reconstruction of the 3D arborescence. In the reconstruction techniques which employ a topographic model of this type, reconstruction necessarily has to be performed largely by hand. On the contrary, in the present invention, the entire process can be automatic.

FIG. 7 shows in comparison the contribution made by the invention in the case of the same structure. In this figure, it has been shown in the first place that the AIV artery was generally located in an interventricular plane IV whilst the circumflex artery was located in an auriculoventricular plane AV. The reference constituted by the planes IV and AV is then used to qualify structurally each of the secondary arteries which are joined to the AIV artery and to the CX artery. In this structural modelization, the knowledge that the AIV and CX arteries are located at the surface of an ellipsoid 48 is therefore abandoned. With respect to the reference IV-AV, one then determines on the other hand the directions 49 to 54 known respectively as forward, rearward, upward, downward, to the right and to the left. These directions make it possible for example to qualify the septal arteries S as being generally oriented downwards from the AIV artery. Similarly, diametral arteries D will be designated as downward and forward, starting from the AIKJ artery. On the other hand, the lateral arteries L joined to the CX artery will be designated as rearward.

It can accordingly be understood with reference to FIG. 5 that it is possible to assign to each segment to be reconstructed a label which is representative of a segment of an artery in the model. This label will have at least in the case of one of its moments the qualifications forward, rearward, upward, etc . . . which have been retained for the artery concerned. It then becomes possible to find out which of the segments 39, 40, 45 or 46 conform in their orientation to the label thus proposed. It is noted in passing that the common trunk in the case of the heart is substantially included in the plane IV of the AIV artery.

Reference being made to FIGS. 8 and 9, the procedure adopted for initializing the reconstruction process in accordance with the invention will now be explained. The three-dimensional starting point as well as the direction of travel at the origin can be fixed by hand. They can also be found automatically by making use of a procedure based on the properties of the images. In fact, the aortic artery AA has a grey level which is much higher than all the other blood vessels by virtue of its size. It is therefore possible to start automatically on a segment which belongs to this aortic artery in each image in projection. To this end, the segment for which the grey level is the highest is chosen from among all the segments.

FIG. 8a shows the skeletonized images obtained respectively in the aforementioned planes 3 and 5. Let $P_{1,j}$ and $P_{2,j}$ be the projections in the planes 3 and 5 of the starting point which has the highest contrast in each image. It is assumed that these two points are homologous to each other and represent a point $P_0$ of the structure to be reconstructed. The point $P_{1,j}$ belongs to a first straight-line element $D_{1,j}$ extending from $P_{1,j}$ to $P_{1,j+1}$ of the root segment of the tree. The same applies to $P_{2,j}$ and $D_{2,j}$. Normally, one seeks the homolog of the point $P_{1,j+1}$ which belongs to the image in the plane 3, the homolog being located in the image in the plane 5. Let $P'_{2,j+1}$ be this point. If $P'_{2,j+1}$ belongs to $D_{2,j}$ (comprised between $P_{2,j}$ and $P_{2,j+1}$), it is possible to reconstruct a first 3D vector from the points $P_{1,j} - P_{1,j+1}$ and $P_{2,j} - P'_{2,j+1}$. FIG. 8b shows this reconstructed vector V. On the other hand, if $P'_{2,j+1}$ is not comprised between $P_{2,j}$ and $P_{2,j+1}$, it is decided to seek the homolog of $P_{2,j+1}$ (image in the plane 5) on the segment $D_{1,j}$ (image in the plane 3). When this has been established, it is postulated that $P'_{2,j+1}$ has been validated. This point has accordingly been found. There is introduced a new straight-line element $P'_{2,j+1} - P_{2,j+1}$ which it is sought to put in correspondence with the straight-line element $P_{1,j+1} - P_{1,j+2}$ of the image in the plane 3. The procedure described in the foregoing is reiterated until detection of an end of segment in one of the views.

Unfortunately, the structural calibration of the equipment, in particular the exact knowledge of the different angles of projection, and similar errors of measurement, may lead to uncertainties as to whether homologous points belong to the straight lines $D_{1,j}$ or $D_{2,j}$. There is experienced in this case a failure in the search for the homologous points: $P'_{2,j+1}$ is external to $D_{2,j}$ and $P'_{1,j+1}$ is external to $D_{1,j}$. FIG. 9 shows a complementary procedure to be employed. In this case, $P'_{2,j+1}$ as well as $P'_{1,j+1}$ do not exist. As a result, $P_{1,j+1}$ and $P_{2,j+1}$ do not have identified homologs. It is then sought to reconstruct a 3D vector from the two straight-line elements $D_{1,j}$ and $D_{2,j}$. It is observed that $D_{1,j}$ is contained in a plane $\pi_1$ defined on the one hand by $D_{1,j}$ and on the other hand by the source 2. Similarly, $D_{2,j}$ is contained in a plane $\pi_2$ defined by $D_{2,j}$ and the source 4. The support of the vector 55 which is sought is the line of intersection of the two planes $\pi_1$ and $\pi_2$. The origin of the vector is known since it corresponds to the projections of $P_{1,j}$ and $P_{2,j}$ which are already known to be homologous. It is decided that the end of the reconstructed segment 55 corresponds by approximations due to the errors either to $P_{1,j+1}$ or to $P_{2,j+1}$. The choice can be made on a criterion of length of the 3D vector. Preferably, the shortest is adopted.

In the case of the heart, the two main CX and AIV branches derived from the common AA trunk characterize the planes. The CX forms a circular arc defining a plane which is substantially orthogonal to the plane containing the AIV. The two starting segments in each plane correspond in one case to the CX and in the other case to the AIV. They are resolved into straight-line elements. Consideration is given to the first straightline element of the segments. The procedure for calculating the 3D vectors corresponding to each segment is identical in its principle to that described in the foregoing in the case of a single 3D vector. The new problem is (as shown in FIG. 5) that there is ambiguity in regard to belonging of the segments. There are then constructed the four 3D vectors, only two of which are the solution.

The criterion of choice of the acceptable solution is based on the hypotheses related to the model. In accordance with these hypotheses, one of the branches, namely the AIV branch in the present instance, has good continuity with the common trunk. In contrast, the tree structure of the blood-vessel system results in the fact that the second branch, namely the CX branch in this case, is distant from the direction parallel to that of the common trunk. It is therefore possible to eliminate the reconstructed 3D vector pair which would not possess in addition a label on the one hand to the rear (for the AIV) and on the other hand to the right (for the CX).

At the end of this step, there are therefore provided two 3D vectors permitting a first estimation of the AV and IV planes. If one moves along the common trunk towards the first bifurcation (point 47) the invariants of the anatomic model make it possible to consider as established the following elements. The common trunk gives rise to two branches, namely the CX branch and the AIV branch. The AIV branch is in continuity with the common trunk. The CX branch is practically orthogonal to the AIV branch at the point of bifurcation. The 3D vector calculated earlier which verifies the property of continuity will receive an AIV label. The other will receive a CX label provided that it verifies the property of orthogonality. If this last-mentioned property is not verified, the reverse designation is attempted. In the event of failure of these two solutions, it may be decided to take another model into consideration.

After initialization, one chooses to follow one of the branches entirely, for example the CX branch. Followup of the first segment of the CX branch is identical with follow-up performed for the common trunk. The plane of the CX is reestimated at each end of segment of the CX. A reestimation of this plane can be made after detection of a first point of connection to the CX. This point of connection can be the bifurcation corresponding to the first lateral branch or to an intersection with a blood vessel. The condition for initiating calculation of reestimation of the plane is that the curvature observed on all the points of the CX exceeds a predetermined threshold value. In order to reestimate the plane, one searches for a plane which provides the best approximation (in the sense of least squares) of all the 3D points of the CX. Calculation of the normal to this plane is carried out again. This reestimation calculation can also be performed after each connection point.

Analysis of the first bifurcation is identical with the case of initialization. It is sought to obtain pairing and labeling with respect to the known model. There will be employed the criteria evaluated on the standard anatomic model, according to which the first bifurcation encountered on the CX corresponds to the start of a lateral branch and to continuation of the CX. The starting segment of the CX is in continuity with the arrival segment of the same CX and the starting segment of the lateral branch is behind the segments of the CX. From this it is automatically determined which segment belongs to the CX and which segment belongs to the lateral artery.

When the plane of the CX is known, it is possible to know the normal vector NIV to the plane. Similarly, it is possible to know the normal vector N AV to the plane AV of the AIV artery. It is possible to verify simply which segment belongs to the CX and which segment belongs to the lateral artery by effecting the scalar product of the two vectors of the successor segments and of the $N_{AV}$ vector. The largest scalar product is in principle that of the CX.

The study of the segments which are considered to belong to the CX is then continued. Data relating to the lateral branch are stored in memory for subsequent reprocessing as soon as one arrives at the end of the CX. The end of the CX is detected by identification of a point without successor in at least one of the planes of the image. The AIV branch is reconstructed in the same manner (with possible reestimation of the plane of the AIV at each stage). The branches left in the standby state are also reconstructed, for example the lateral branch which is detected at the time of travel on the CX.

The operation of the method according to the invention calls for acquisition of two images, if possible simultaneously. Different sources of errors exist such as calibration of the radiology system or sampling of the images and the uncertainties of segmentation derived from skeletonization. The fact of working on the basis of images having very different angles of view permits the achievement of much higher accuracy of reconstruction. The speed of the procedure is due to the highly structured description of the data and to the high participation of the symbolic model. The method is applicable to any other arborescent vascular structure whenever the corresponding anatomic 3D model is acquired and is integrated with the system.

In cardiac applications, this rapid method can permit the study of the blood vessel system in motion on the basis of images acquired in two incidences and at different stages of cardiac motion. In practice, reconstruction of arborescence of the image has a time duration of the same order as skeletonization and is of the order of 3 seconds. In the case of models other than the left ventricle of the heart, they can be constructed by making use on the one hand of standard anatomic knowledge and on the other hand preferably of an interactive filar reconstruction generator. This type of generator is available in the form of a logic system. One example is the logic system known as Generateur Interactif de Structures Vasculaires 3D (Interactive Generator for 3D Vascular Structures) available at the University of Rennes, Laboratoire des Signaux et Images en Medecine, Faculte des Sciences, Campus de Beaulieu, 35042 Rennes Cedex, France. For characterization of the models, it is endeavored in the first place to find principal planes which may or may not be orthogonal. There are then described by means of the interactive generator the different segments encountered with qualifications mentioned earlier, namely continuity, forward, rearward, upward, downward, to the right, to the left, and so on. If this is permitted by the anatomic study of individuals it is possible to construct a number of models in the case of a given arborescent structure. In the case of the left ventricle, there have thus been constructed three models, namely one which can be employed in 80% of the cases and corresponding to balanced vascularization and two others which can each be employed in 10% of the cases and corresponding to preponderant left or right vascularizations.

Moreover, taking into account the planes IV and AV, the importance of which is thus clearly apparent, it will be preferable to acquire the images in projection in directions contained in planes which bisect principal planes of the model, taking into account the position of the patient in the machine. The structural model can naturally be completed insofar as the criterion is sufficiently sound, by topographic (quantitative) information. Thus, in the case of a segment having a number N belonging to the AIV (or to the CX) and joined to a forwardly-oriented segment N-1, it will be possible to add a label supplement in the form: expected length comprised between a and b, mean grey level (equivalent to the diameter) comprised between c and d. Verification of the accuracy of the label can also consist of an additional verification that the reconstructed segment has in fact an adequate length and grey level. These topographic verifications can be optional and can become critical only in the event of failure of the structural identification.

We claim:

1. A method of computer-aided construction of a three-dimensional image of a three-dimensional physical arborescence, said physical arborescence being constituted by segments of same material and corresponding to an a priori three-dimensional structural model being memorized in a computer and being constituted by image segments provided with labels, each label being constituted by a coded signal, comprising the steps of:

acquiring by a physical process at least a first image and a second image having two dimensions of said arborescence to be constructed, these 2-dimensional images being obtained by projection of said arborescence to be reconstructed in two different orientations, said images being constituted by contiguous segments;

choosing a reference constituted by a cartesian system, said cartesian system being associated with two first principal planes corresponding to two particular branches of said arborescence, said labels comprising meanings forward, backward, upward, downward, rightward, and leftward, according to an orientation of said segment with regard to said principal planes of said cartesian system;

reconstructing a first segment of said physical arborescence starting from said corresponding two-dimensional projection images of said first segment;

assigning a label to said first segment;

checking the correctness of said assignment by comparing a coded signal of said assigned label of said first segment to a coded signal of the label of a corresponding segment in a model, wherein said segment is accepted or refused depending on the result of said checking; and reiterating the operation for a following segment.

2. A method according to claim 1, wherein the first and second images are acquired each time by means of two exposures of the arborescence to X-rays, the exposures being differentiated by the fact that the arborescence is subjected to a radiological contrast-enhancing product during one of these exposures.

3. A method according to claim 1, wherein, in order to acquire the first and second images, the images are skeletonized-segmented by a follow-up method, each segment comprising a numeral which is assigned thereto, the coordinates of each of its extremities, a mean grey level, the direction of said segment, and the numbers, numerals, directions, grey level of its predecessors and successors.

4. A method according to claim 3, wherein the follow-up method comprises, a stage of location of the central axes of the segments in each image by following the peaks of the detected signals; and a stage of measurement of contours of the segment.

5. A method according to claim 1, wherein the steps of assigning, checking and reiterating are effected by data-processing.

6. A method according to claim 1, wherein each label comprises a code which is representative of a bifurcation from which said segment is derived.

7. A method according to claim 6, wherein the structural model is completed by a topographic model, the label being such as to contain data relating to the diameter of the segments and to their size.

8. A method according claim 6, wherein the reference is changed from one segment to another.

9. A method according to claim 1, wherein each label further comprises a code which is representative of an upstream segment to which the segment is joined.

10. A method according to claim 9, wherein in the event of failure of verification that the epipolar straight line intersects the image of said segment in the second image, there are calculated directing vectors of a line of intersection of the two planes containing respectively the origin of the projections and the projected images of the segment.

11. A method according to claim 1, wherein the reconstruction of the first segment comprises,
determining in the first and second images a pair of homologous points which are representative of a starting point att he first end of said first segment;
projecting in the second image an epipolar straight line of the other end of said segment in the first image;
verifying that said epipolar straight line intersects the image of said segment in the second image; and
retaining as the other end of said segment the point which corresponds to said intersection.

12. A method according to claim 11, wherein reconstruction of a following segment comprises,
reiterating the preceding operations by choosing the end of the first segment as a starting point of the following segment.

13. A method according to claim 1, wherein
in order to assign a label to an adjacent segment, there is assigned thereto a label corresponding to an assumed position of said segment, said assumed position being deduced in a hypothesis is checked; and
in the event of failure of the verification, the operation is repeated by assigning another label.

14. A method according to claim 1, wherein said method further comprising:
constructing a plurality of models;
choosing one of said models; and
in the event of failure of the reconstruction, choosing another model.

15. A method according to claim 1, wherein construction of the model is managed by a filar reconstruction interactive generator from an anatomic model.

16. A method according to claim 1, wherein the first and second images are obtained by projection in orientations which bisect angles delimited by two principal planes, namely the planes IV and AV in the case of the heart.

17. A method according to claim 1, wherein in a reconstruction of arterial arborescence of a left ventricle of a heart, thee are sought substantially orthogonal planes considered to belong to the AIV and to the CX.

* * * * *